US008752432B2

(12) United States Patent
Meitzler et al.

(10) Patent No.: US 8,752,432 B2
(45) Date of Patent: Jun. 17, 2014

(54) SELF DIAGNOSTIC COMPOSITE ARMOR

(75) Inventors: Thomas J. Meitzler, Troy, MI (US);
Ivan Wong, Novi, MI (US); Thomas P. Reynolds, Warren, MI (US); Samuel E. Ebenstein, Southfield, MI (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 522 days.

(21) Appl. No.: 13/173,766

(22) Filed: Jun. 30, 2011

(65) Prior Publication Data

US 2013/0000408 A1      Jan. 3, 2013

(51) Int. Cl.
*G01N 29/12*          (2006.01)

(52) U.S. Cl.
USPC ............................................. 73/588; 73/582

(58) Field of Classification Search
CPC ............................. G01N 29/043; G01N 29/12
See application file for complete search history.

(56) References Cited

U.S. PATENT DOCUMENTS

| | | | |
|---|---|---|---|
| 3,023,609 A | 3/1962 | Schubring | |
| 3,043,132 A | 7/1962 | Schubring | |
| 4,379,401 A | 4/1983 | San Miguel | |
| 5,195,046 A | 3/1993 | Gerardi et al. | |
| 5,847,259 A | 12/1998 | Hu | |
| 5,970,843 A | 10/1999 | Strasser et al. | |
| 6,332,390 B1 * | 12/2001 | Lyons | 89/36.02 |
| 6,856,918 B2 | 2/2005 | Dubois et al. | |
| 7,076,695 B2 | 7/2006 | McGee et al. | |
| 7,180,302 B2 | 2/2007 | Kelsey et al. | |
| 7,643,945 B2 | 1/2010 | Baklanov et al. | |
| 2003/0101007 A1 | 5/2003 | Dubois et al. | |
| 2008/0294354 A1 | 11/2008 | Zhu et al. | |
| 2009/0027229 A1 * | 1/2009 | Fortson et al. | 340/870.07 |
| 2010/0050308 A1 * | 3/2010 | Roberson et al. | 2/2.5 |

OTHER PUBLICATIONS

Alan Bryman and Melissa A. Hardy, Handbook of Data Analysis, Book, p. 230.
Meitzler, Wong, Bryk, Reynolds & Ebenstein, Damage Detection in Composite plate Armor Using Ultrasonic Techniques (U), US Army RDECOM—TARDEC.
J.W. Gillespie, Jr., Repair of Composite Integral Armor, University of Delaware, 2002 NCMS CMTA Symposium.
Incident Control Systems, What is Composite Armor?, Incident Control Systems website.
Wikipedia, Composite Armour, wikipedia.org.
Holmquist Rajendran, Templeton & Bishnoi: TACOM RDE Center A Ceramic Armor Material Database, Storming Media.

(Continued)

*Primary Examiner* — Hezron E Williams
*Assistant Examiner* — Paul West
(74) *Attorney, Agent, or Firm* — Thomas W. Saur; David L. Kuhn; Luis Miguel Acosta

(57) ABSTRACT

A system incorporating sensor enhanced composite armor structure. The structure has one layer including ceramic tiles and ceramic-material transducers, wherein the ceramic tiles and the transducers fit closely together so that the one layer is ballistically windowless. The structure has other layers composed of armor material stacked with the one layer, the one layer and the other layers forming a plate which as a unit has a set or group of fundamental frequencies. The system includes logic means to analyze only signals resulting from vibrations transmitted from the one transducer to the other transducer through the one layer. The logic means thereby derives a signal fingerprint which characterizes a state of damage to the plate.

4 Claims, 6 Drawing Sheets

(56) References Cited

OTHER PUBLICATIONS

Rank Enterprises, Inc., Vehicle Armor, wwwrankarmor.com.
Piezoelectric Products, Ceramic Components, www.omegapiezo.com.
Dr. Thomas J. Meitzler, Sensor Enhanced Armor and Non-Destructive Evaluation Laboratory, Briefing to MSU CVRC, RDE Command, Warren, MI.
Wikipedia, Chobham Armor, wikipedia.org.

\* cited by examiner

SELF DIAGNOSTIC COMPOSITE ARMOR

GOVERNMENT INTEREST

The invention described here may be made, used and licensed by and for the U.S. Government for governmental purposes without paying royalty to me.

BACKGROUND OF THE INVENTION

1. Field of the Invention

The invention lies within the art of designing a composite armor plate. The invention also lies within the art of signal processing as used in conjunction with nondestructive testing.

2. Background Art

One aspect of the invention relates to nondestructive testing of manufactured articles or other work pieces of interest. A common form of nondestructive testing is subjecting a work piece to vibrations at selected amplitudes and frequencies and thereafter analyzing the vibrational responses of the work piece. Typically transducers on the work piece transmit signals or signal patterns that are processed by a computer algorithm or by logic circuitry to determine whether the work piece is flawed. A relatively early example, circa 1958, of this sort of nondestructive testing is U.S. Pat. No. 3,023,609 to Schubring. Often in nondestructive testing, work pieces known to be flawless or at least acceptable are tested in order to establish a standard or baseline against which subsequent test results for later-produced work pieces can be compared. For example, see U.S. Pat. No. 5,195,046 to Girardi et al.

Numerous data analysis techniques historically have been used to process data that is derived from sensor output signals in nondestructive testing. A comprehensive treatment of data analysis techniques is found in *Handbook of Data Analysis* by Alan Bryman and Melissa A. Hardy published in 2004 by SAGE Publications Ltd, this book being available on line at http://books.google.com/books. Aside from Gerardi, there are innumerable other examples where acoustic or vibrational nondestructive testing is performed on work pieces using well-known data analysis methods. One example is U.S. Pat. No. 7,076,695 to McGee et al. The data analyzing techniques in McGee include, inter alia, a Chi-square test, elimination of non significant data, normalization, and centering of data. The McGee methods are adaptable to production environments or post production testing of manufactured items during the items' lifetime. Application of acoustic or vibrational non destructive testing techniques to a plate of composite armor and the use data analysis to interpret vibrational responses of the plate has been shown and discussed in the article "Damage Detection in Composite Plate Armor Using Ultrasonic Techniques" by Meitzler et al released Aug. 17, 2009 and available on line at http://oai.dtic.mil.

Another aspect of the invention relates to the structure composite armor generally and relates particularly to composite armor having at least one layer comprised of ceramic tiles. An overview of various composite armor structures is seen in "Repair of Composite Integral Armor by J. W. Gillespie, Jr. presented at the NCMS CMTA Symposium at Jacksonville, Fla., Apr. 16-18, 2002. This and other references show at least one layer in a composite armor plate comprised of closely spaced ceramic tiles. Many on-line sites discuss composite armor structures. By way of example these sites include a discussion of Chobham armor at http://en.wikipedia.org/wiki/Chobham_armor and a commercial site http://www.rankarmor.com/no_vehicle.php. See also U.S. Pat. No. 5,790,843 to Strasser et al., which shows various ballistically protective materials used in an integrated armor plate structure.

A further aspect of the invention relates to the use of piezoelectric transducers in composite armor structure. The aforementioned article, "Damage Detection in Composite Plate Armor Using Ultrasonic Techniques" shows the use of piezoelectric sensors with a ceramic composite armor plate. Ceramic piezoelectric sensors with customized geometries can be obtained from commercial sources. See, e.g., the Omega Piezo Technologies web site at http://www.omegapiezo.comiceramic_components.html.

SUMMARY OF THE INVENTION

The invention is a self-diagnostic armor system wherein a composite armor plate has embedded transducers and wherein the system has a signal processing mechanism to interpret output from the transducers and thereby determine the health of the plate. One layer of the plate is formed by combining ceramic tiles having a regular polygonal outline with transducers of ceramic material specially shaped to match the thickness and polygonal outline of the tiles. The transducers and tiles fit closely together to form a ballistically windowless plate layer. One of the transducers receives specially chosen input signals and responds by sending ultrasonic waves or vibrations travelling mainly parallel to the ballistically windowless layer at selected frequencies and amplitudes. Another of the transducers, responding essentially only to waves or vibrations travelling parallel to the ballistically windowless layer, sends output signals in response to the vibrations of the ballistically windowless layer. There is a bonding agent between adjacent ceramic tiles and between adjoining ceramic tiles and transducers, the agent enhancing the passage of vibrations from the one transducer to the other transducer through the ceramic tiles. The composite armor plate has additional layers of armor material stacked with the ballistically windowless layer. The ballistically windowless layer and the other layers form a plate which vibrates and has a set of characteristic fundamental frequencies. The system includes logic means, such as a computer or logic circuitry, to analyze the transducer output signals. The logic means analyzes signals resulting essentially only from vibrations parallel to the ballistically windowless layer to derive a signal fingerprint characterizing an undamaged plate. The logic means can use a subsequent set of vibrations to determine a change in the output vibrations of the plate and comparing the output vibrations to the fingerprint to thus detect initial damage to the plate. The logic means can continue to analyze the vibrations after the initial change in the fingerprint to determine a second, later change in the plate's vibrations and thus detect additional damage to the plate. The system includes transducer damage detection means to sense cessation of transducer function, thereby detecting damage to the plate in the form of damage to one or more of the transducers.

DETAILED DESCRIPTION OF THE PREFERRED EMBODIMENT(S)

Definitions and Terminology:

The following definitions and terminology are applied as understood by one skilled in the appropriate art. The singular forms such as "a," "an," and "the" include plural references unless the context clearly indicates otherwise. For example, reference to "a material" includes reference to one or more of such materials, and "an element" includes reference to one or more of such elements.

As used herein, "substantial" and "about", when used in reference to a quantity or amount of a material, dimension, characteristic, parameter, and the like, refer to an amount that is sufficient to provide an effect that the material or characteristic was intended to provide as understood by one skilled in the art. The amount of variation generally depends on the specific implementation. Similarly, "substantially free of" or "essentially free of" or the like refers to the lack of an identified composition, characteristic, or property. Particularly, assemblies that are identified as being "essentially free of" are either completely absent of the characteristic, or the characteristic is present only in values which are small enough that no meaningful effect on the desired results is generated.

Concentrations, values, dimensions, amounts, and other quantitative data may be presented herein in a range format. One skilled in the art will understand that such range format is used for convenience and brevity and should be interpreted flexibly to include not only the numerical values explicitly recited as the limits of the range, but also to include all the individual numerical values or sub-ranges encompassed within that range as if each numerical value and sub-range is explicitly recited. For example, a size range of about 1 dimensional unit to about 100 dimensional units should be interpreted to include not only the explicitly recited limits, but also to include individual sizes such as 2 dimensional units, 3 dimensional units, 10 dimensional units, and the like; and sub-ranges such as 10 dimensional units to 50 dimensional units, 20 dimensional units to 100 dimensional units, and the like.

Figure 1:
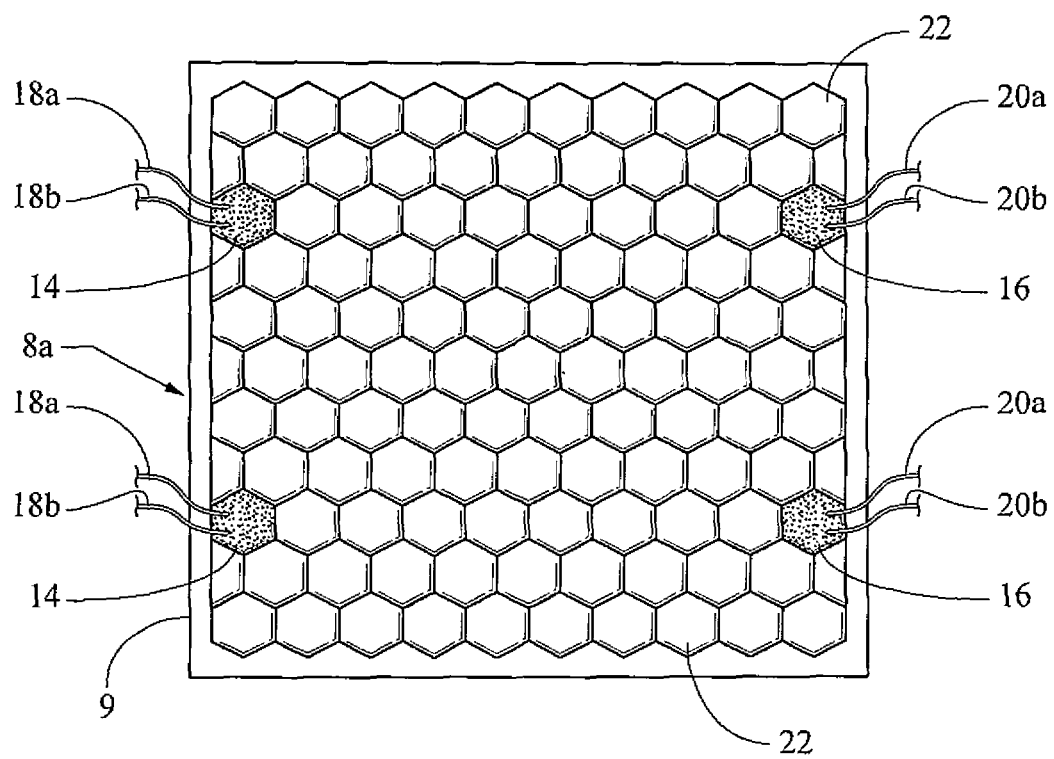
FIG. 1 is a top elevational view of a component layer or plate that is part of a sensor enhanced composite armor plate.
Figure 2:
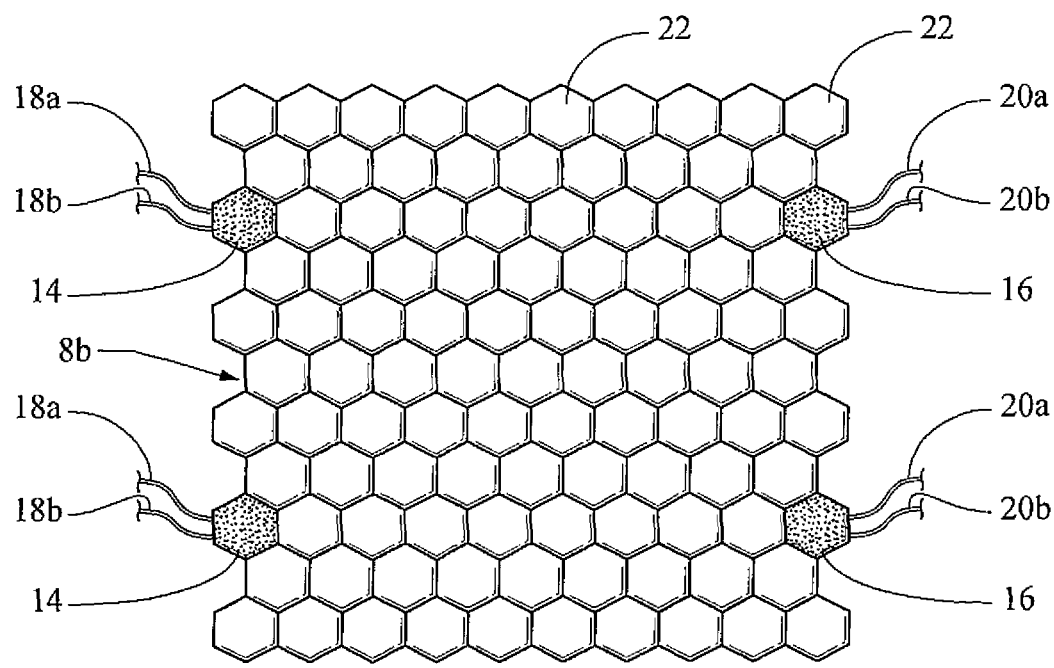
FIG. 2 is a top elevational view of an alternate embodiment of the component layer or plate shown in FIG. 1.

In FIG. 1 is shown a component plate 8a that forms one layer of a composite armor plate or other composite armor structure. Plate 8a is comprised of ceramic tiles 22 that have a regular polygonal outline such as a square or octagon but most typically have a hexagonal outline as seen in FIGS. 1 and 2. Tiles 22 fit closely together and may be pressed together so as to form a continuous layer through which acoustic signals can easily travel. A surrounding border 9 or edge of armor steel or other suitable material may optionally be provided on plate 8a. A component plate 8b without the surrounding border is shown in FIG. 2. Preferably tiles 22 are pressed together and are bonded together by an adhesive that enhances the passage of vibrations, ultrasonic signals or other acoustic signals between the tiles. Bonding materials such as Evercoat® Sea Repair Marine Adhesive Glue, can be used for this purpose. This latter product was found to have resiliency when a composite armor panel was subjected to high G acceleration during ballistic impact. Other epoxies that may be acceptable for given applications include Loctite® Professional Extra Time Epoxy, Loctite® Professional Heavy Duty Epoxy and Permatex® Black Silicon Adhesive Sealant.

Plate 8a includes piezoelectric transducers 14 and 16 at opposed edges of the plate. These transducers are made of ballistically protective ceramic material which affords armor protection, and the transducers have the same shape and thickness as ceramic tiles 22. The transducers fit closely to with tiles 22. The transducers can be pressed and bonded to the tiles in the same way that the tiles are pressed and bonded to each other. The tiles and transducers form a continuous, unapertured layer that is ballistically windowless in that the layer has no weak points or openings that would denigrate the layer's ability to deter projectiles or plasma streams. Transducers 14 at one edge of plate 8a are "sending transducers" and generate vibrations which travel throughout plate 8a. Transducers 14 respond to input electrical signals of selected frequency and amplitude from a signal generator 112 (shown in FIG. 6). Transducers 14 and 16 are selected so as to be sensitive to the fundamental frequencies of plate 10. By using an impedance analyzer one can measure both the minimum impedance frequency and the maximum impedance frequency of the transducers using a well known experimental procedure. In this fashion it is possible to select or design transducers having a frequency range that includes the fundamental frequencies of plate 10.

The transducers are connected to the signal generator by lines 18a and 18b. Lines 18a and 18b are connected at selected points on transducers 14 so as to maximize ultrasonic wave travel in plate 8a from one edge thereof toward the other edges. That is, ultrasonic wave or vibration travel is maximized parallel to the general plane in which plate 8a lies. On the opposite side of plate 8a from sending transducers 14 are receiving transducers 16, which produce electrical signals in response to the vibrations emanating from a sending transducer 14. Transducer 16 responds essentially only to waves or vibrations travelling parallel to the ballistically windowless layer that originate from transducer 14. Typically one of transducers 14 is paired with one of transducers 16 and only one pair of transducers is operating at a given time. It is possible to use only one pair of transducers for plate 8a or to use one or more additional pairs as a redundancy.

Figure 3:
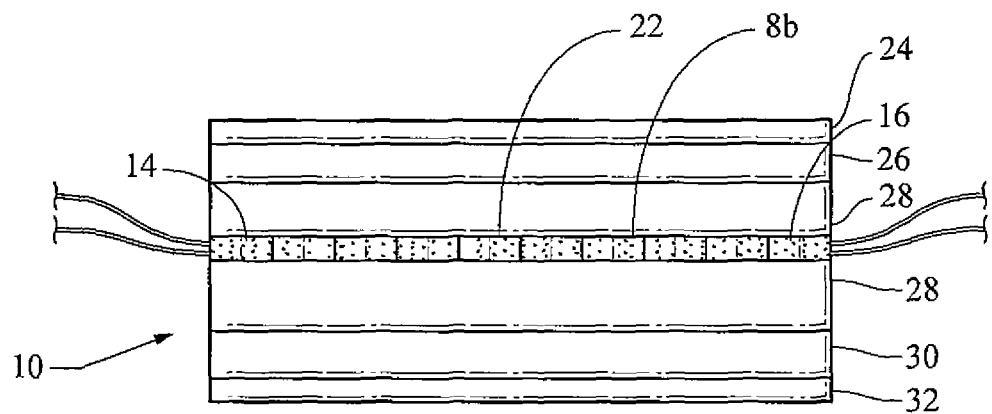
FIG. 3 a side elevational view of a sensor enhanced composite armor plate including the component armor plate in FIG. 2.
Figure 4:
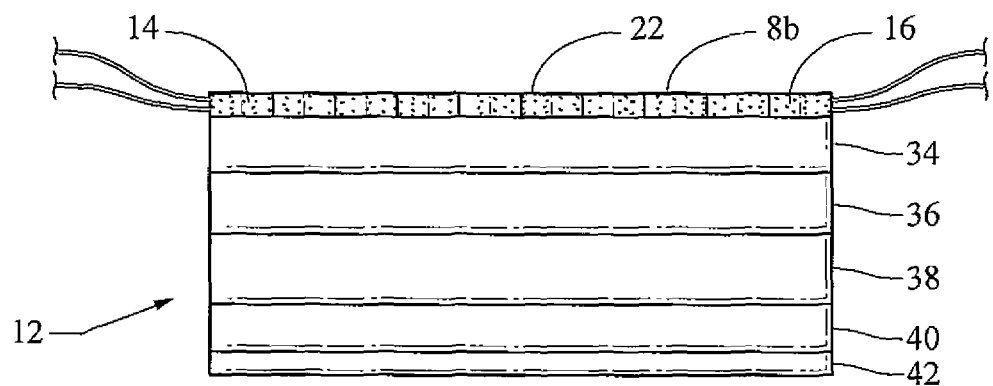
FIG. 4 is a side elevational view of an alternate embodiment of the composite armor plate shown in FIG. 3.

FIGS. 3 and 4 show side views of composite armor plates that incorporate component plate 8b. In FIG. 3, composite armor plate 10 is comprised of a plurality of layers of armor material. The layers are bonded together such that plate 10 vibrates and has resonant frequencies and a fundamental frequency along both a length and width dimension which is characteristic of plate 10. In our invention, for a rectangular composite armor plate, we prefer to use the frequencies along the longer, or length, dimension of the plate. The individual layers 24, 26, 28, 30 and 32 can be comprised, for example, of armor grade steel or aluminum, boron carbides, aluminum nitrides, aluminum oxides, silicon carbides or fiber reinforced ceramic material, as well as other known armor-component materials. For the purposes of our invention it is not necessary that the layers 24, 26, 28, 30 and 32 (FIG. 3) have particular thicknesses or that they be stacked in a particular order. Likewise it is not necessary that layers 34, 36, 38, 40 and 42 of composite armor plate 12 (FIG. 4) have particular thicknesses or that they be stacked in a particular order. However it is necessary that one of the layers of composite armor plate 10 include the structure component plate 8*a* or 8*b*; plate 8*a* or 8*b* can be the top or bottom layer of composite armor plate 10 or can be one of the layers between the top and bottom of the composite armor plate.

Referring again to FIG. 3, when sending transducer 14 vibrates, it sends ultrasonic signals though the component plate to receiving transducer 16. It has been found that damage to any layer of composite armor plate 10 will affect the transmission of ultrasonic signals from transducer 14 to transducer 16. Thus, if composite armor plate 10 is undamaged and transducer 14 sends a particular selection of ultrasonic signals, transducer 16 will receive a first, unique, identifiable set of signals that correspond to an undamaged composite armor plate. As discussed later in conjunction with FIG. 6, this first set of signals is used to derive a fingerprint unique to plate 10 which indicates that plate 10 is undamaged. Let us say that layers 24 and 26 are then damaged by ballistic impact of a projectile and transducer 14 thereafter resends the same particular set of ultrasonic signals. Plate 10 will have a variation in its fundamental and resonant frequencies that affect the transmission of ultrasonic signals through component plate 8*b* and consequently transducer 16 will receive a second set of signals that indicate damage to composite armor plate 10. If component plate 22 is damaged, then the fundamental and resonant frequencies of composite plate 10 will alter in a similar fashion and the set of ultrasonic signals received by transducer 16 will again vary from the set of signals received when the composite armor plate is undamaged. Thus, by monitoring signal transmission though the component plate 22, it is possible to detect damage to any part of the composite plate.

It will be understood that damage to plate 10, and particularly damage to component plate 8*a*, is detected by two means. The first means is by monitoring the variation in signals received by transducer 16 as described above, and this means is used when transducers 14 and 16 remain undamaged. However, the transducers form part of the armor structure of composite armor plate 10 and may suffer damage in a battle scenario. Damage to the transducers will be detected simply when signal transmission between the transducers is degraded or stopped altogether. It is possible and may be preferred to incorporate in known fashion a fault detection mechanism to differentiate whether stoppage of transducer signals is caused by a problem with the transducers or whether stoppage of these signals caused by another problem in the circuitry of which the transducers are part. It may also be preferred to have redundant pairs of transducers 14 and 16 so the health condition of plate 10 can be verified if transmission fails between a primary pair of transducers.

Figure 5:
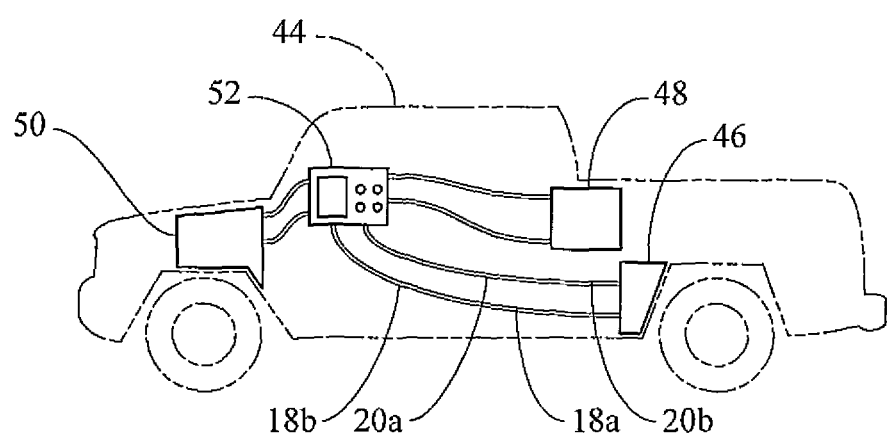
FIG. 5 diagrammatically shows a vehicle having a plurality of sensor enhanced composite armor plates and a system for monitoring the health of the plates.

In FIG. 5 is shown an outline of a vehicle 44 on which vehicle armor plates 46, 48 and 50 are installed. These plates are shown to have varied, nonrectangular outlines, although plates with rectangular outlines can be used as well. The vehicle plates are composite armor plates that have a layered structure such as that shown in FIG. 3 or FIG. 4 and each vehicle plate has resonant frequencies and fundamental frequencies and a fingerprint unique to the plate indicative of that plate's undamaged condition. It will be noted that two composite armor plates having exactly the same structure will have fingerprints that are essentially the same. Typically, however, vehicles have composite armor plates need plates of differing shape to most effectively and efficiently protect the vehicle. It is thus advantageous that composite plates of varied shapes can be fingerprinted by the method described below in connection with FIG. 6. Likewise, damage to plates of varied shapes can be detected after they are fingerprinted according to this same method.

Preferably mounted in the cab area of vehicle 44 is a control unit 52. Unit 52 communicates with plates 46, 48 and 50 through lines such as those at 18*a*, 18*b*, 20*a* and 20*b* between control unit 52 and plate 46. Controller 52 includes a signal generating device which sends input electrical signals of chosen frequencies and amplitudes to sending transducers 14 (not shown in FIG. 5) in or on the vehicle armor plates. Controller 52 also includes a signal processor which receives output signals from receiving transducers 16 (not shown in FIG. 5) in or on these plates. Controller 52 further includes an electronic memory that stores the fingerprint and location on vehicle 44 of each vehicle armored plate. Optionally, the fingerprint for each plate can be stored on a memory chip on or embedded in the plate.

Analysis of Transducer Signals

Figure 6:
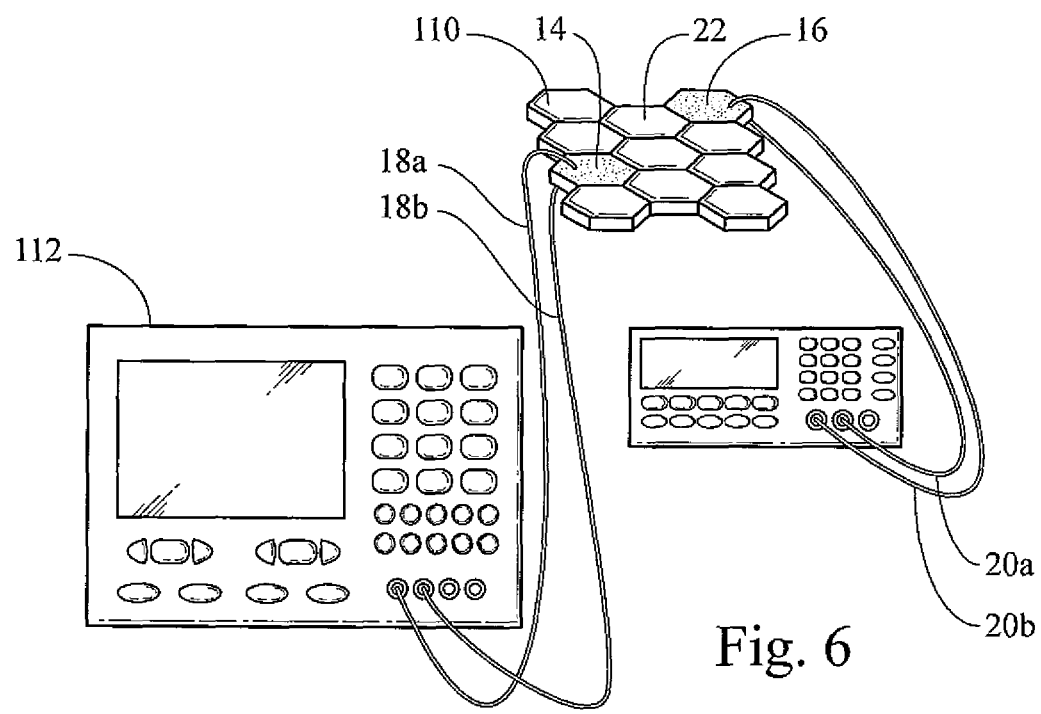
FIG. 6 diagrammatically shows the testing arrangement by which a fingerprint for an undamaged plate of armor is derived.

In FIG. 6 is diagrammatically shown the testing arrangement by which a fingerprint for an undamaged plate of armor is derived and by which a subsequent testing of the plate is done to determine whether the plate has been damaged. For convenience, the plate to be tested is represented at 110 as a section comprised of the ceramic tiles 22 shown in FIGS. 1 through 4. However, it will be understood the plate to be tested will normally be a fully assembled composite armor plate with a plurality of layers such as those plates shown at 10 and 12 in FIGS. 3 and 4, respectively. Plate 110 will include one or more of the ceramic piezoelectric sending transducers 14 and will include one or more receiving ceramic piezoelectric transducers 16. The testing arrangement includes a signal generating device 112 which sends input electrical signals of chosen frequencies and amplitudes to sending transducer 14 via lines 18*a* and 18*b*. Preferably, the frequencies are in the ultrasonic range. Sending transducer 14 vibrates in response to the electrical signals and these vibrations, along with variations to the transmitted signals caused by internal reflections at boundaries and interfaces, are transmitted to receiving transducer 16, which produces output electrical signals characteristic of the vibrations. The output electrical signals are transmitted via lines 20*a* and 20*b* to data acquisition device such as a signal processor 114, to either derive a healthy-plate fingerprint or to subsequently detect plate damage by comparing the plate's current vibrations to the healthy-plate fingerprint. Note that the above-described procedure can also be used to recalibrate a composite armor plate's fingerprint after initial damage to the plate which is relatively minor or acceptable in a mission critical circumstance. This can be achieved by testing the plate several times as was initially done when the plate was known to be undamaged. The plate can then be monitored to determine if additional damage has occurred.

In the interest of insuring a full and enabling disclosure of the invention, enumerated here is a step-by-step explanation of a preferred method of processing signals for the diagnosis of the condition of a composite armor plate.

1. Start with a composite armor plate known to be undamaged or healthy.

2. During a set of tests, send waves of various frequencies from one transducer (14) in the plate to another transducer (16) in the plate. Do this for selected intervals in a given frequency range. For example, the frequency range can be from 1 kHz to 500 kHz. The intervals can be frequencies at 1 kHz, 2 kHz, 3 kHz . . . 500 kHz. A selected number of readings in volts for the frequency responses, also denoted as amplitudes, can be taken at each interval from the receiving transducer's output.

3. For the set of tests, calculate the root mean squares (RMS) for the amplitudes at each interval.

4. For the set of tests, calculate the average value of the amplitudes for each interval or frequency to produce an "average amplitude vs. frequency" curve.

5. For each individual test in the set of tests, find the minimum amplitude. Then for the set of tests, calculate the average minimum amplitude value.

6. For each individual test subtract the average minimum amplitude value from each of the average values of the amplitudes calculated in step 4 to create centered average values of the amplitudes.

7. For the set of tests, sum together all the squares of the centered average values of the amplitudes for each interval or frequency and divide each centered average amplitude by the square root of the sum, thus creating centered normalized average amplitude values, and then forming a centered normalized amplitude vs. frequency curve.

8. For the set of tests, and for each frequency in a test, calculate the standard deviation of the normalized average values to produce a "standard deviation vs. frequency" curve.

9. For the set of tests, sort and rank the values of the centered normalized amplitude values from highest to lowest.

10. For the set of tests, add the squares of the centered normalized amplitude values with the highest average values together until the sum of these squared values reaches or exceeds a threshold percentage of the summed squares of average amplitude values from step 7. Then set the remaining average values to zero. This creates a fundamental frequency vector wherein the fundamental frequencies are those associated with the centered normalized average amplitudes with the highest values.

Figure 7:
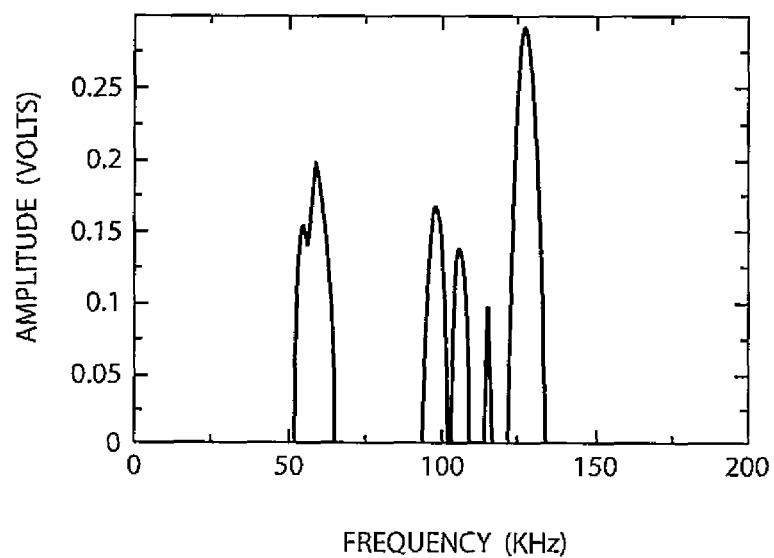
FIG. 7 shows a graph representing the fingerprint of a healthy, undamaged composite armor plate after the plate has been tested using the arrangement in FIG. 6.

11. The next step is done for each individual test. For each frequency that has been identified as a fundamental frequency in step 10 subtract the average minimum amplitude value derived in step 6 from the corresponding amplitude obtained from the test. Note that "corresponding" means being at the same interval or frequency. The foregoing subtractions create a set of differences which are centered test amplitude values associated with the fundamental frequencies. A typical graphic representation of these values is shown at FIG. 7. The results of this operation using readings from all of the individual tests would also be typified by FIG. 7, though minor variations would occur because of using a larger database. In either case, FIG. 7 depicts a typical example of the plate's initial, "healthy," fingerprint.

12. For each difference found in step 11, divide the difference by the corresponding standard deviation found in step 8. This produces a result value for each fundamental frequency associated with an individual test.

13. For each fundamental frequency in the test, determine whether the result value is greater than a tolerance value. Ignore result values that are less than the tolerance value.

The tolerance value is usually 3.0. The tolerance value here is from statistical control chart theory. In a classical statistical control chart, we say a process is under control as long as all values are within the control limits, which are usually within 3 sigmas from the average. Since we are using normal scores, this corresponds to plus or minus 3. By changing the tolerance value we make the metric either more or less able to detect small changes in vibration. By using a lower tolerance value the metric is more able to detect subtle changes in the vibrations, and conversely a high tolerance value makes the metric less responsive, but more stable.

14. For each test, for result values greater than the tolerance value, square the result value. Sum the squared result values; take the square root of the sum; divide the square root of sum by the total number of intervals in the frequency range of step 2. This obtains a metric for a given test.

15. For the set of tests, calculate the standard deviation of the metrics, thereby deriving a fingerprint standard deviation value useful to determine a state of health of the plate in a subsequent set of trials;

16. There are now a valid fingerprint or fingerprint file and associated data for the composite armor plate. It is possible to perform subsequent trials to see whether the plate has been damaged The first step in these trials is to send waves at the fundamental frequencies derived in Step 10 through the composite plate from the one transducer to the other transducer. Typically there are 3 trials to guarantee stability of the results. However each trial is individually analyzed.

17. For each trial compare the current plate vibrations to the valid fingerprint file. Do this by first subtracting the average minimum amplitude of step 6 from the current plate vibrations at the fundamental frequencies and then continue processing the current plate vibrations in accordance with steps 12-15 above. Compare the metrics and standard deviations resulting from this latter operation to the metric for the valid fingerprint.

Figure 8:
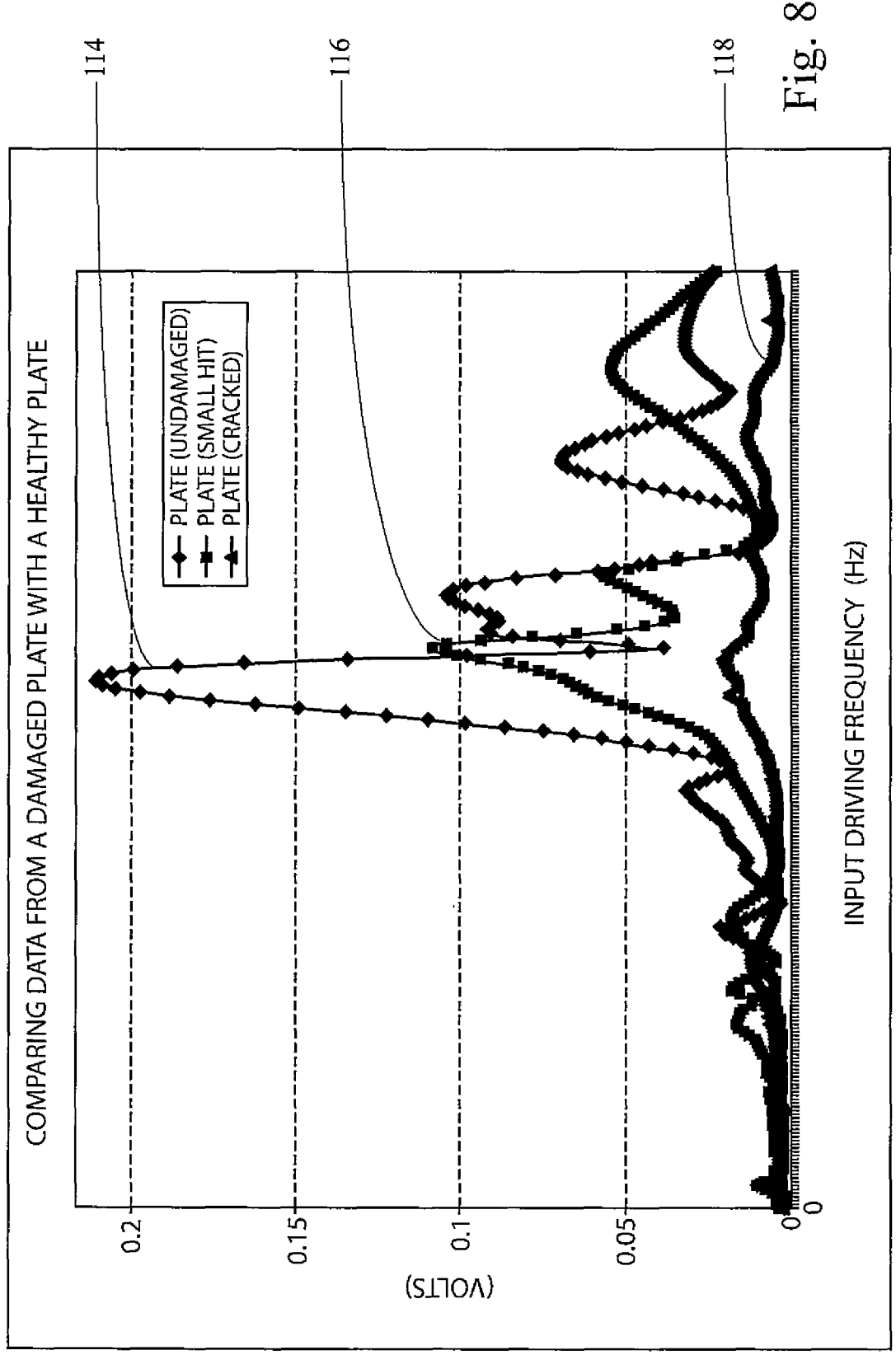
FIG. 8 shows the results of experiments done on similar composite armor plates wherein the first plate was undamaged, the second plate had slight damage and the third plate had severe damage.

Relevant to the foregoing analysis is FIG. 8, which shows the results of experiments done in the 0-125 Hz domain on three composite armor plates having the same structure. The first composite armor plate was undamaged, and the second composite armor plate had a relatively-sight-damage condition (a small projectile hit) wherein the plate could still provide significant ballistic protection. The third composite armor plate had a relatively-severe-damage condition and was cracked, and could provide essentially no ballistic protection. For each plate in the experiment the same set of input signals were given to a sending transducer 14 in a fashion similar to step 2 above. The sending transducers 14 for each plate responded to vibrations from the sending transducers and sent sets of output signals represented by the curves in FIG. 8. Curve 114 indicates an undamaged plate condition, curve 116 indicates a relatively-slight-damage plate condition and curve 118 indicates a relatively-severe-damage plate condition. FIG. 8 illustrates that it is possible, using our invention, to differentiate among an undamaged condition for a composite armor plate, a later relatively slight-damage condition of that plate, and a still later relatively-severe-damage condition of that plate.

Figure 9:
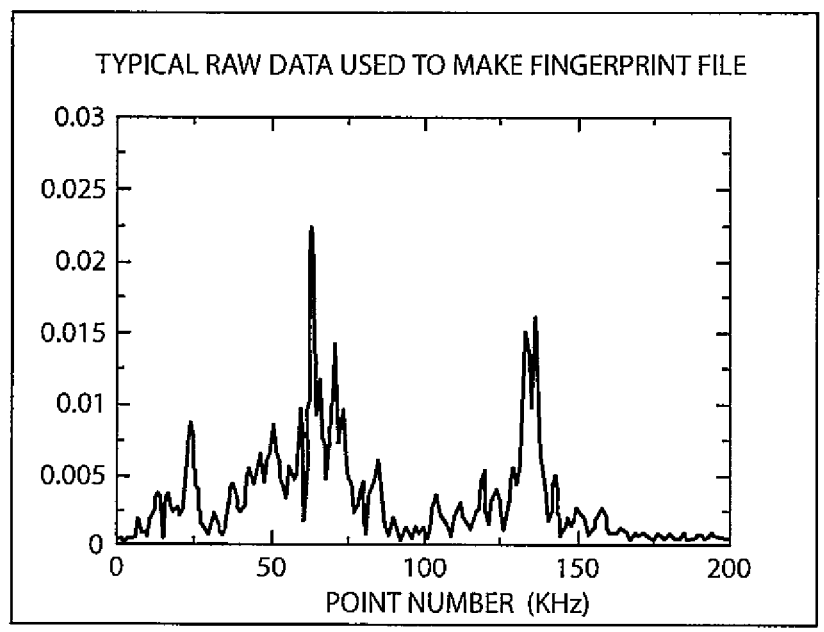
FIG. 9 shows the full spectrum of raw ultrasonic frequencies received during testing by a receiving transducer.
Figure 10:
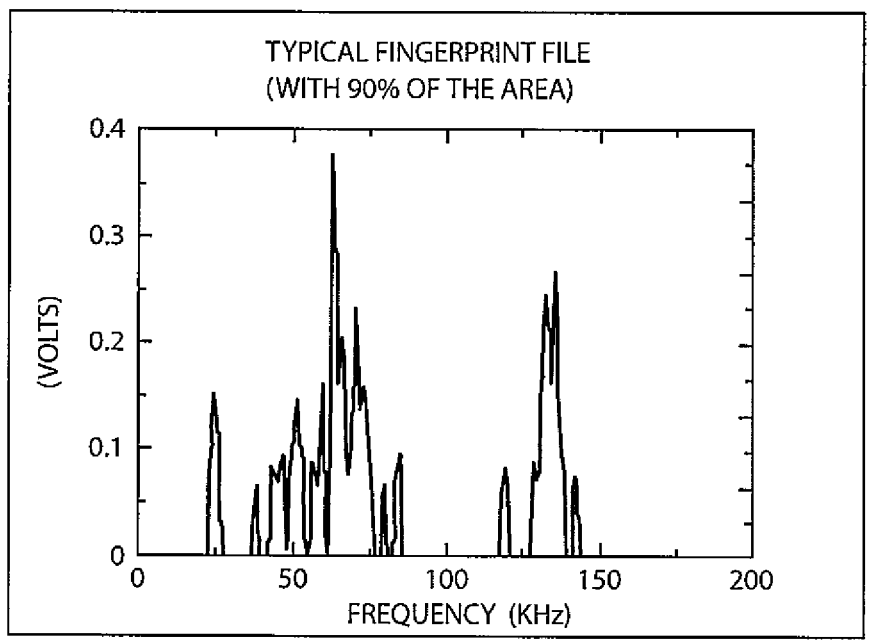
FIG. 10 shows the part of the spectrum of FIG. 9 that is used to make the ultrasonic fingerprint of the armor plate.
Figure 11:
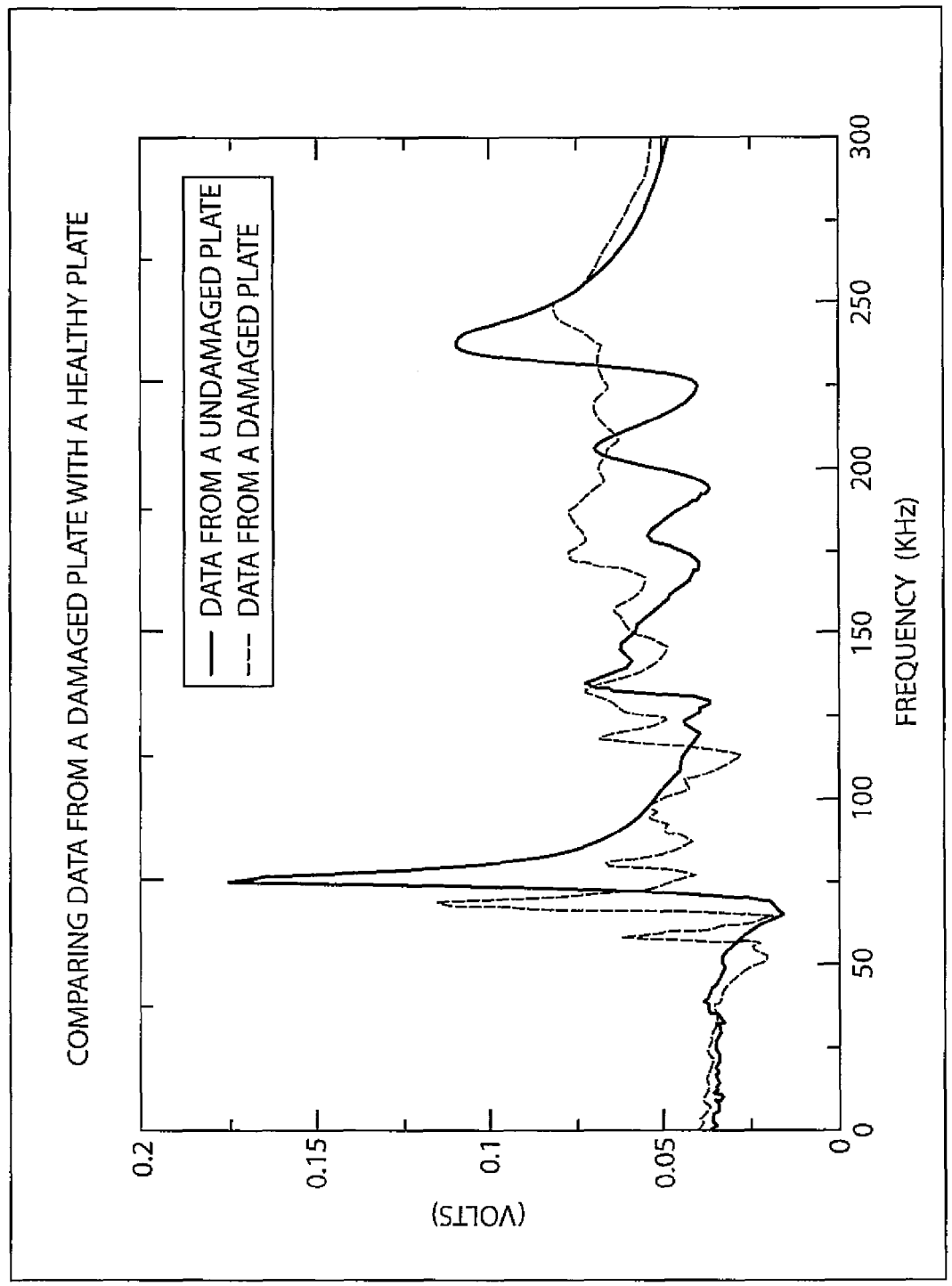
FIG. 11 shows a comparison of the spectrum from an undamaged armor plate and a damaged armor plate.

The utility of the foregoing analysis can be further appreciated by viewing the graphs in FIGS. 9, 10 and 11. FIG. 9 shows the full spectrum of ultrasonic frequencies received by receiving transducer 16 in raw, unprocessed signal form. FIG. 10 shows the part of the spectrum from FIG. 9 that is used to make the ultrasonic fingerprint of the armor plate. FIG. 11 shows a comparison of the spectrum from an undamaged armor plate and a damaged armor plate. For the purposes of discussing FIGS. 9, 10 and 11, "undamaged" means that the armor plate has been shot once but has not been catastrophically damaged and retains essentially all of its original ballistic protection capability, whereas a damaged armor plate is one that is catastrophically damaged and provides essentially no ballistic protection. When comparing the spectrum of the damaged armor plate to the spectrum of the undamaged armor plate one can see that there has been a shift in the location of the major peaks and that some of the peaks have vanished.

Various alterations and modifications will become apparent to those skilled in the art without departing from the scope and spirit of this invention and it is understood this invention is limited only by the following claims.

What is claimed is:

1. A system including a self diagnostic composite armor structure, comprising:
   ceramic tiles in one layer of the armor structure, the tiles having a regular polygonal outline;
   transducers in the one layer, one of the transducers sending vibrations detected by another of the transducers, the transducers being of ceramic material and having a same thickness and a same regular polygonal outline as the regular polygonal outline of the ceramic tiles;
   wherein the other of the transducers responds essentially only to vibrations travelling parallel to the one layer;
   wherein the ceramic tiles and the transducers fit closely together so that the one layer is a ballistically windowless layer;
   a bonding agent between adjacent ceramic tiles and between adjoining ceramic tiles and transducers, the agent enhancing the passage of vibrations from the one transducer to the other transducer through the ceramic tiles;
   other layers of armor material stacked with the one layer so that the one layer and the other layers form a plate which vibrates as a unit and has characteristic fundamental frequencies;
   logic means to analyze signals resulting from vibrations transmitted from the one transducer to the other transducer parallel to the plate through the one layer to derive a signal fingerprint characterizing an undamaged plate, the logic means capable of using the vibrations to determine an initial change in the fingerprint and to thus detect initial damage to the plate, and determine the health of the entire plate;
   wherein the logic means can continue to analyze vibrations after the initial change in the fingerprint to determine a subsequent change in the received vibrations and detect subsequent additional damage to the plate; and
   transducer damage detection means to detect cessation of transducer function, thereby detecting damage to the plate in the form of damage to one or more of the transducers.

2. The self diagnostic armor system of claim 1 wherein:
   a plurality of the plates are disposed on a vehicle;
   the plates vary in size and shape;
   the other layers in a first plate have different materials and layer thicknesses than a second plate;
   a computer on board the vehicle contains a record of the signal fingerprint and location of each plate on the vehicle.

3. A self diagnostic composite armor system, comprising:
   ceramic tiles of uniform shape pressed together in one layer of the armor structure, the tiles having a regular polygonal outline;
   piezoelectric transducers in the one layer at opposed edges of the one layer, one of the transducers sending vibrations detected by another of the transducers, the transducers being of ballistically protective ceramic material and having a same thickness and a same regular polygonal outline as the regular polygonal outline of the ceramic tiles;
   wherein the ceramic tiles and the transducers fit closely together so that the one layer is a continuous, unapertured, ballistically windowless layer;
   a bonding agent between adjacent ceramic tiles and between adjoining ceramic tiles and transducers, the agent enhancing the passage of vibrations from the one transducer to the other transducer through the ceramic tiles;
   other layers of armor material stacked with the one layer so that the one layer and the other layers form a plate which vibrates as a unit and has characteristic fundamental frequencies;
   logic means to analyze signals resulting from vibrations transmitted from the one transducer to the other transducer travelling parallel to the plate through the one layer to derive a signal fingerprint characterizing an undamaged plate, the logic means capable of using the vibrations to determine an initial change in the signal fingerprint and to thus detect initial damage to the plate;
   wherein the logic means can continue to analyze the vibrations after the initial change in the fingerprint to determine a subsequent change in the fingerprint and detect subsequent additional damage to the plate; and
   transducer damage detection means to detect cessation of transducer function, thereby detecting damage to the plate in the form of damage to one or more of the transducers.

4. The self diagnostic composite armor system of claim 3 wherein the transducers are selected so as to be sensitive to the fundamental frequencies of the composite armor system by using an impedance analyzer to determine the frequency range of the transducers.

* * * * *